(12) United States Patent
Jugl et al.

(10) Patent No.: US 12,390,598 B2
(45) Date of Patent: Aug. 19, 2025

(54) SUPPLEMENTARY DEVICE FOR AN INJECTION DEVICE

(71) Applicant: Sanofi, Paris (FR)

(72) Inventors: Michael Jugl, Frankfurt am Main (DE); Günther Sendatzki, Frankfurt am Main (DE); Christian Rehbein, Frankfurt am Main (DE)

(73) Assignee: Sanofi, Paris (FR)

( * ) Notice: Subject to any disclaimer, the term of this patent is extended or adjusted under 35 U.S.C. 154(b) by 971 days.

(21) Appl. No.: 17/296,010

(22) PCT Filed: Nov. 14, 2019

(86) PCT No.: PCT/EP2019/081297
§ 371 (c)(1),
(2) Date: May 21, 2021

(87) PCT Pub. No.: WO2020/104285
PCT Pub. Date: May 28, 2020

(65) Prior Publication Data
US 2022/0016352 A1    Jan. 20, 2022

(30) Foreign Application Priority Data

Nov. 23, 2018 (EP) .................................. 18306560

(51) Int. Cl.
*A61M 5/315* (2006.01)
*A61M 5/31* (2006.01)

(52) U.S. Cl.
CPC ...... *A61M 5/31551* (2013.01); *A61M 5/3155* (2013.01); *A61M 5/31568* (2013.01); *A61M 2005/3126* (2013.01); *A61M 5/31593* (2013.01)

(58) Field of Classification Search
CPC ............ A61M 5/31568; A61M 5/3155; A61M 5/31551; A61M 5/31553; A61M 5/31546; A61M 5/31565; A61M 5/3159
See application file for complete search history.

(56) References Cited

U.S. PATENT DOCUMENTS

| 2018/0008778 A1 | 1/2018 | Erbstein |
| 2018/0021520 A1* | 1/2018 | Cerman .............. A61M 5/3155 604/189 |

(Continued)

FOREIGN PATENT DOCUMENTS

| CN | 102740907 | 10/2012 |
| CN | 107206172 | 9/2017 |

(Continued)

OTHER PUBLICATIONS

PCT International Search Report and Written Opinion in International Application No. PCT/EP2019/081297, dated Dec. 5, 2019, 11 pages.

(Continued)

*Primary Examiner* — Emily L Schmidt
*Assistant Examiner* — Samuel J Marrison
(74) *Attorney, Agent, or Firm* — Bond, Schoeneck & King, PLLC

(57) ABSTRACT

A supplementary device for an injection device is disclosed. The injection device has a control dial that is rotatably mounted about an axis at a proximal end of the injection device, and the supplementary device is attachable to the control dial. The supplementary device includes a sleeve adapted to be positioned over the control dial when the supplementary device is attached to the injection device. The supplementary device also includes an axial attachment member arranged such that insertion of the control dial into the sleeve moves the axial attachment member from an initial position that permits axial movement of the control (Continued)

dial into the sleeve, into an engagement position in which the axial attachment member engages the control dial to axially attach the supplementary device to the control dial.

13 Claims, 15 Drawing Sheets

(56) References Cited

U.S. PATENT DOCUMENTS

| | | | |
|---|---|---|---|
| 2018/0147362 A1* | 5/2018 | Arenas Latorre | G16H 20/17 |
| 2018/0154086 A1 | 6/2018 | Toporek et al. | |
| 2021/0093795 A1* | 4/2021 | Byerly | A61M 5/31551 |
| 2022/0088317 A1* | 3/2022 | Marcoz | A61M 5/31568 |

FOREIGN PATENT DOCUMENTS

| | | |
|---|---|---|
| EP | 2182456 | 5/2010 |
| JP | 2012-519026 | 8/2012 |
| JP | 2018-505028 | 2/2018 |
| WO | WO 2010/098928 | 9/2010 |
| WO | WO 2011/067187 | 6/2011 |
| WO | WO 2016/128426 | 8/2016 |
| WO | WO 2016/146434 | 9/2016 |
| WO | WO 2018/013419 | 1/2018 |
| WO | WO 2020/104285 | 5/2020 |

OTHER PUBLICATIONS

International Preliminary Report on Patentability in International Application No. PCT/EP2019/081297, dated Jun. 3, 2021, 9 pages.
Notice of Reason(s) for Rejection, JP Patent Application No. 2024-019880, dated Oct. 22, 2024, pp. 1-6 (with pp. 3-6 being a translation).

* cited by examiner

SUPPLEMENTARY DEVICE FOR AN INJECTION DEVICE

CROSS REFERENCE TO RELATED APPLICATIONS

The present application is the national stage entry of International Patent Application No. PCT/EP2019/081297, filed on Nov. 14, 2019, and claims priority to Application No. EP 18306560.6, filed on Nov. 23, 2018, the disclosures of which are incorporated herein by reference.

TECHNICAL FIELD

The present disclosure relates to a supplementary device for an injection device, for example a data collection device for attachment over a control dial of an injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a control dial and observing the actual dose from a dose window or display of the insulin pen. The dose is then injected by inserting the needle into a suited skin portion and pressing an injection button of the insulin pen.

To be able to monitor insulin injection, for instance to prevent false handling of the insulin pen or to keep track of the doses already applied, it is desirable to measure information related to a condition and/or use of the injection device, such as for instance information on the injected insulin dose.

SUMMARY

A first aspect of the present disclosure provides a supplementary device for an injection device, said injection device comprising a control dial that is rotatably mounted about an axis at a proximal end of said injection device, and wherein the supplementary device comprises:
- a sleeve adapted to be positioned over said control dial when the supplementary device is attached to said injection device; and,
- an axial attachment member arranged such that insertion of said control dial into the sleeve moves the axial attachment member from an initial position that permits axial movement of said control dial into the sleeve, into an engagement position in which the axial attachment member engages said control dial to attach the supplementary device to said control dial.

In some embodiments the axial attachment member in the engagement position can be adapted to engage the control dial such that axial movement of the control dial relative to the sleeve is restricted.

The supplementary device may further comprise a rotational coupling member arranged to rotationally couple the sleeve to said control dial such that rotation of the supplementary device causes rotation of the control dial. The axial attachment member and the rotational coupling member may be different features of the supplementary device; however it can be appreciated that in some embodiments the axial attachment member and the rotational coupling member can be formed as a single component.

The control dial may comprise one or more axially extending formations protruding from said control dial, and wherein the rotational coupling member may comprise one or more grooves arranged to engage said one or more formations to rotationally couple the sleeve to said control dial.

The one or more grooves are adapted to receive formations having different sizes and/or shapes such that the supplementary device can be used with various injection devices. Advantageously, the grooves do not need to tightly fit formations of the various control dials because the axial attachment member holds the supplementary device on the control dial, and the grooves only provide rotational coupling.

The axial attachment member may be arranged to engage a distal edge of said control dial. In some examples, the distal edge of the control dial includes the distal edge of one or more formations on the control dial.

In some examples, the axial attachment member may comprise a clamp having a plurality of arms, and wherein in the initial position said control dial can move between the arms, and wherein in the engagement position the arms are pressed against said control dial for axial attachment.

The plurality of arms may protrude from a base. For instance, the plurality of arms may protrude from a base ring, although it should be recognized that in other embodiments the base may have a different shape and may, for instance, be U-shaped or may be a solid shape. In some embodiments, the base is, for example, circular, oval or square.

The arms may extend distally from the base and abut an inner circumferential surface of the sleeve such that proximal movement of the base into the sleeve moves the arms from the initial position to the engagement position.

The distal ends of the arms may be bent inwardly such that in the engagement position the distal ends of the arms press against said control dial.

In some examples, the axial attachment member may comprise a snap portion arranged to engage with an edge of said control dial in a snap fit. The snap portion may be arranged to engage with a distal edge of said control dial. In some examples, the distal edge of the control dial includes the distal edge of one or more formations on the control dial.

In other examples, the sleeve may comprise a circumferentially extending groove and the axial attachment member may comprise a resiliently deformable ring disposed in the groove. In this example, the resiliently deformable ring is arranged such that in the engagement position the resiliently deformable ring is deflected outwardly and grips said control dial.

The deformable ring may be adapted to cut into said control dial in the engagement position. The resiliently deformable ring may comprise one or more cutting teeth. The deformable ring may include a stepped inner edge that matches formations on the control dial.

The supplementary device may be a data collection device. In some examples, the data collection device includes a second portion that is rotatably coupled with the sleeve. At least part of the second portion may be movable axially relative to the first portion. The data collection device may also include a sensor arrangement configured to detect rotation of the second portion relative to the sleeve. The data collection device may include a processor configured to, based on the detected movement, determine a medicament amount expelled by the injection device.

The data collection device may also include a sensor arrangement configured to detect vibrations and/or sounds originating from the movement of the second portion relative to the sleeve or from a user. The data collection device may include a processor configured to, based on the detected vibrations and/or sounds, determine a medicament amount expelled by the injection device.

The data collection device when installed can monitor quantities and times of medicament delivery from the injection device. For example, medicament quantities can be transmitted, e.g. to a smartphone, and/or displayed on a display of the data collection device.

In some embodiments the axial attachment member may be made from a resilient material, which in the initial position can be biased in a direction so as to permit axial movement of the control dial into the sleeve. The axial attachment member may be made from a metal.

In some embodiments the diameter of the attachment member can be reduced in the engagement position relative to the initial position. The sleeve may have a geometric profile to urge the attachment member to have a smaller diameter in the engagement position relative to the initial position such as ramps, guides, tapered portions or a thickening of the sleeve wall.

In some embodiments the supplementary device can be removed from the injection device, the attachment member and/or rotational coupling member moving from the engagement position back to the initial position.

In some embodiments, the injection device has a distal end that is opposite to the proximal end. In some embodiments, the distal end of the injection device is the end of the injection device where a medicament delivery element, for example, a needle, is located.

In some embodiments, the sleeve is configured to rotationally couple to the said control dial such that that rotation of the supplementary device causes rotation of the control dial. Optionally, the sleeve comprises a rotational coupling such as a rotational coupling member on the inner sleeve to rotationally couple the sleeve to the control dial.

In some embodiments, the control dial of the injection device is for setting a dose, for example, for setting a dose of medicament to be delivered by the injection device.

In some embodiments, the sleeve comprises a cavity for receiving at least a portion of the control dial.

In some embodiments, the supplementary device is configured to be positioned over said control dial when the supplementary device is attached to said injection device such that the supplementary device rotates together with the control dial.

In some embodiments, the supplementary device is configured to be positioned over said control dial when the supplementary device is attached to said injection device such that the supplementary device does not contact portions of the injection device that do not rotate together with the control dial, for example, a housing to which the control dial is rotatably mounted. However, a skilled person would recognize that in other embodiments, the supplementary device may abut said non-rotating portion and may move relative to said non-rotating portion when the control dial rotates. For example, the supplementary device may abut and move over an exterior surface of said housing as the control dial rotates. Alternatively, a first portion of the supplementary device may rotate together with the control dial whilst a second portion of the supplementary device remains stationary relative to the remainder of the injection device (the control dial rotating relative to said second portion of the supplementary device), for example, the second portion being rotatably coupled to the first portion of the supplementary device.

In one embodiment, there is provided a supplementary device for an injection device, said injection device comprising a control dial that is rotatably mounted about an axis at a proximal end of said injection device, and wherein the supplementary device comprises: a sleeve adapted to be positioned over said control dial when the supplementary device is attached to said injection device; and, an axial attachment member arranged such that insertion of said control dial into the sleeve moves the axial attachment member from an initial position that permits axial movement of said control dial into the sleeve, into an engagement position in which the axial attachment member engages said control dial to attach the supplementary device to said control dial, wherein the axial attachment member comprises a clamp having a plurality of arms, and wherein in the initial position said control dial can move between the arms, and wherein in the engagement position the arms are pressed against said control dial for axial attachment, wherein the arms extend distally from a base and abut an inner circumferential surface of the sleeve such that proximal movement of the base into the sleeve moves the arms from the initial position to the engagement position.

In one embodiment, there is provided a supplementary device for an injection device, said injection device comprising a control dial that is rotatably mounted about an axis at a proximal end of said injection device, and wherein the supplementary device comprises: a sleeve adapted to be positioned over said control dial when the supplementary device is attached to said injection device; and, an axial attachment member arranged such that insertion of said control dial into the sleeve moves the axial attachment member from an initial position that permits axial movement of said control dial into the sleeve, into an engagement position in which the axial attachment member engages said control dial to attach the supplementary device to said control dial, wherein the sleeve comprises a circumferentially extending groove and the axial attachment member comprises a resiliently deformable ring disposed in the groove, and wherein the resiliently deformable ring is arranged such that in the engagement position the resiliently deformable ring is deflected outwardly and grips said control dial.

A further aspect of the present disclosure is a method of attaching a supplementary device to an injection device, the injection device being elongate in an axial direction and comprising a control dial that is rotatably mounted at a proximal end of said injection device, and wherein attachment of the supplementary device comprises positioning a sleeve of the supplementary device over said control dial; and, deflecting an axial attachment member into an engagement position in which the axial attachment member engages said control dial to axially attach the supplementary device to said control dial.

In some examples, the axial attachment member may comprise a clamp having a plurality of arms, and wherein in the initial position said control dial can move between the arms, and wherein in the engagement position the arms are pressed against said control dial for axial attachment. The plurality of arms may protrude from a base. For instance, the plurality of arms may protrude from a base ring, although it should be recognized that in other embodiments the base may have a shape other than a ring and may, for instance, be U-shaped or may be a solid shape in cross-section. The base may be, for example, circular, oval or square.

The arms may extend distally from the base and abut an inner circumferential surface of the sleeve such that proximal movement of the base into the sleeve moves the arms from the initial position to the engagement position.

In other examples, the sleeve may comprise a circumferentially extending groove and the axial attachment member may comprise a resiliently deformable ring disposed in the groove. In this example, the resiliently deformable ring is arranged such that in the engagement position the resiliently deformable ring is deflected outwardly and grips said control dial.

Some embodiments will become more fully understood from the detailed description given herein below, wherein below and the accompanying drawings, which are given by way of illustration only, and do not limit the present invention.

BRIEF DESCRIPTION OF THE FIGURES

Examples will now be described with reference to the accompanying figures, of which.

DETAILED DESCRIPTION

The present specification discloses a supplementary device for an injection device. A supplementary device is attachable to an injection device to perform a supplementary function.

In some examples, the supplementary device is a data collection device that is attachable over a control dial at a proximal end of an injection device, such as a pen injector, such as to fit the injection device like a cap. In particular, the data collection device includes a sleeve in which the control dial is received. The sleeve defines a cavity into which the control dial is pushed to attach the data collection device to the injection device. In various examples described herein the data collection device includes an axial attachment member that attaches the data collection device to the control dial to hold the data collection device axially on the injection device. A further rotational coupling member may be provided to rotationally couple the data collection device to the control dial.

When installed over the control dial of the injection device, the data collection device can be manipulated by the user in order to effect operation of the injection device. The data collection device when installed can monitor quantities and times of medicament delivery from the injection device. For example, medicament quantities can be transmitted, e.g. to a smartphone, and/or displayed on a display of the data collection device. In examples, the data collection device, and particularly the attachment features, can be configured to be attached to a series of different injection devices and thus monitor a user's medicament treatment over multiple devices. Moreover, this can be achieved without impeding normal use of the injection device and without obscuring a dosage window of the injection device.

In the following, examples will be described with reference to an insulin injection device. The present disclosure is however not limited to such an application and may equally well be deployed with injection devices that eject other medicaments.

In addition, the following examples will be described with reference to a supplementary device that is a data collection device. However, the present disclosure is not limited to data collection devices and the supplementary device may equally well be a different type of supplementary device for an injection device. For example, the supplementary device attaches to the injection device and performs one or more functions, so as to automate the injection device.

Figure 1:
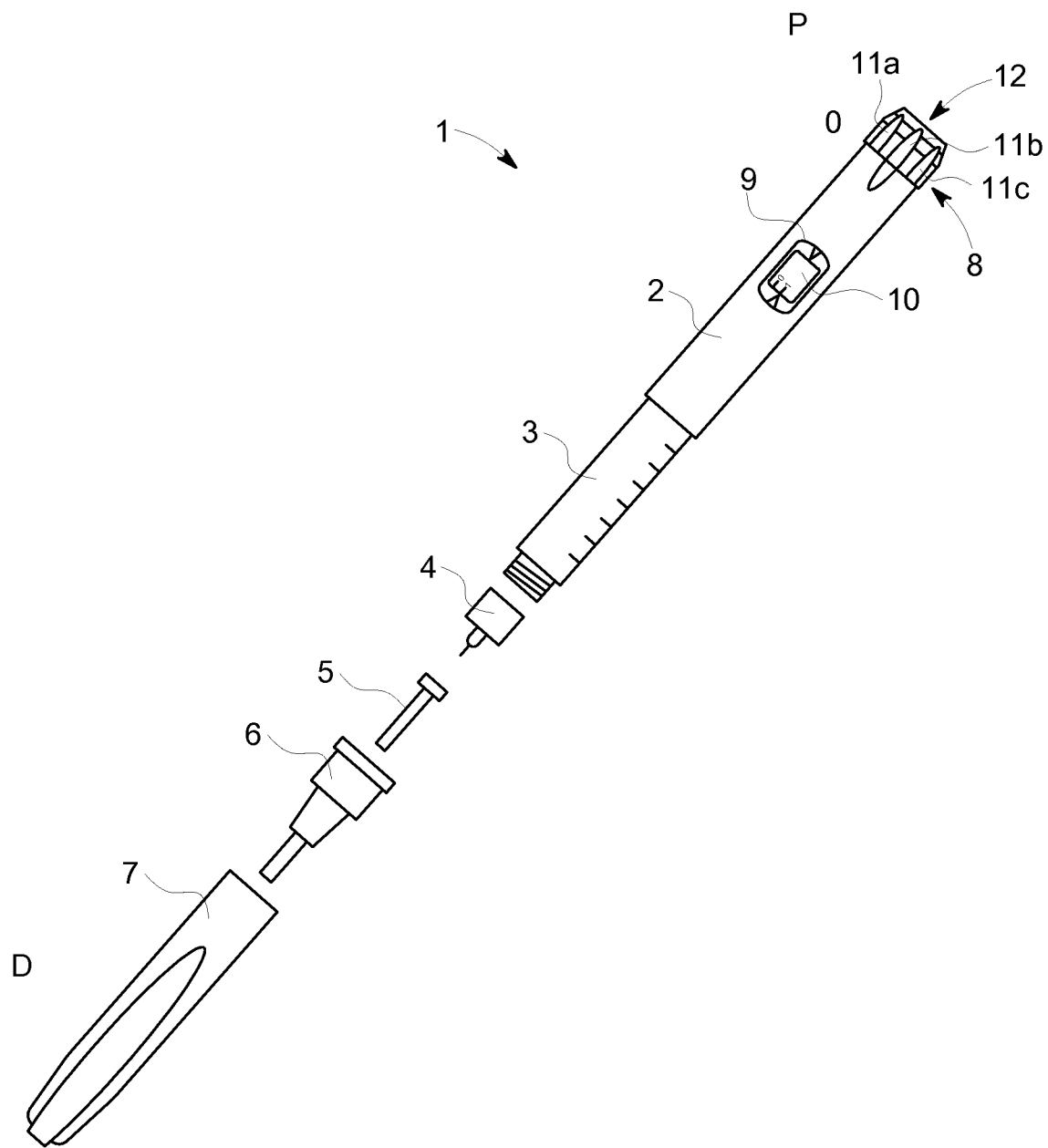
FIG. 1 shows an exploded view of an injection device for use with a data collection device.

FIG. 1 is an exploded view of a medicament delivery device. In this example, the medicament delivery device is an injection device 1, such as Sanofi's SoloSTAR® insulin injection pen.

The injection device 1 of FIG. 1 is a pre-filled, disposable injection pen that comprises a housing 2 and contains an insulin container 3, to which a needle 4 can be affixed. The needle 4 is protected by an inner needle cap 5 and either an outer needle cap 6 or an alternative cap 7. An insulin dose to be ejected from injection device 1 can be programmed, or 'dialed in' by turning a control dial 8, and a currently programmed dose is then displayed via dosage window 9, for instance in multiples of units. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 9 in FIG. 1.

As referred to herein, the distal end D of the injection device 1 is the end of the injection device 1 where the needle 4 is located. The proximal end P of the injection device 1 is the opposite end of the injection device 1, opposite to the needle 4.

The control dial 8 is disposed at a proximal end P of the injection device 1, and the needle 4 is disposed at a distal end D of the injection device 1. The injection device 1 is elongate. In this example, the housing 2 is cylindrical, but the housing 2, and the injection device 1 more generally, may be another elongate shape. The control dial 8 is rotatable about an axis on the injection device 1. The elongate housing 2 of the injection device 1 extends in the axial direction.

The dosage window 9 may be in the form of an aperture in the housing 2, which permits a user to view a limited portion of a number sleeve 10 that is configured to move when the control dial 8 is turned, to provide a visual indication of a currently programmed dose. The control dial 8 is rotated on a helical path with respect to the housing 2 when turned during programming.

In this example, the control dial 8 includes one or more formations 11*a*, 11*b*, 11*c* to facilitate gripping the control dial 8 if no supplementary device is used. The formations 11*a*, 11*b*, 11*c* are described in further detail hereinafter with reference to FIGS. 4A and 4B.

The injection device 1 may be configured so that turning the control dial 8 causes a mechanical click sound to provide acoustic feedback to a user. The number sleeve 10 mechanically interacts with a piston in the insulin container 3. When needle 4 is stuck into a skin portion of a patient, and then injection button 12 is pushed, the insulin dose displayed in display window 9 will be ejected from injection device 1. When the needle 4 of injection device 1 remains for a certain time in the skin portion after the injection button 12 is pushed, a high percentage of the dose is actually injected into the patient's body. Ejection of the insulin dose may also cause a mechanical click sound, which is however different from the sounds produced when using control dial 8.

In this embodiment, during delivery of the insulin dose, the control dial 8 is turned to its initial position in an axial movement, that is to say without rotation, while the number sleeve 10 is rotated to return to its initial position, e.g. to display a dose of zero units.

Injection device 1 may be used for several injection processes until either the insulin container 3 is empty or the expiration date of the medicament in the injection device 1 (e.g. 28 days after the first use) is reached.

Furthermore, before using injection device 1 for the first time, it may be necessary to perform a so-called "prime shot" to remove air from insulin container 3 and needle 4, for instance by selecting two units of insulin and pressing injection button 12 while holding injection device 1 with the needle 4 upwards. For simplicity of presentation, in the following, it will be assumed that the ejected amounts substantially correspond to the injected doses, so that, for instance the amount of medicament ejected from the injection device 1 is equal to the dose received by the user. Nevertheless, differences (e.g. losses) between the ejected amounts and the injected doses may need to be taken into account.

Figure 2:
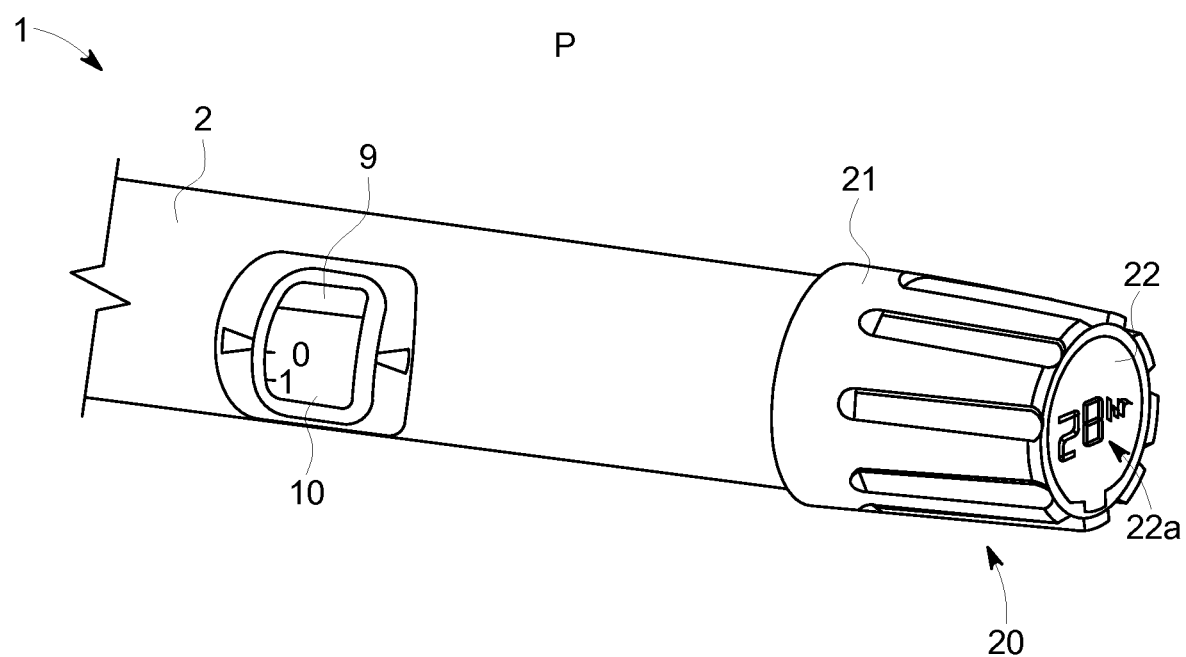
FIG. 2 depicts a data collection device attached to the injection device of FIG. 1.

FIG. 2 is a perspective view of the proximal end P of the injection device 1 when a data collection device 20 is attached. The data collection device 20 includes a housing 21 and an end plate 22 with an optional display 22*a*. The data collection device 20 may take one of a number of different forms, as described below and as shown in the drawings. The data collection device 20 may be used with various injection devices 1 having different control dials 8, as explained further hereinafter.

As shown in FIG. 2, when the data collection device 20 is attached to the injection device 1 it covers the control dial 8 (see FIG. 1) at the proximal end of the injection device 1. As explained above, rotation of the data collection device 20 causes rotation of the control dial 8 (see FIG. 1) to use the injection device 1, as explained above.

Figure 3:
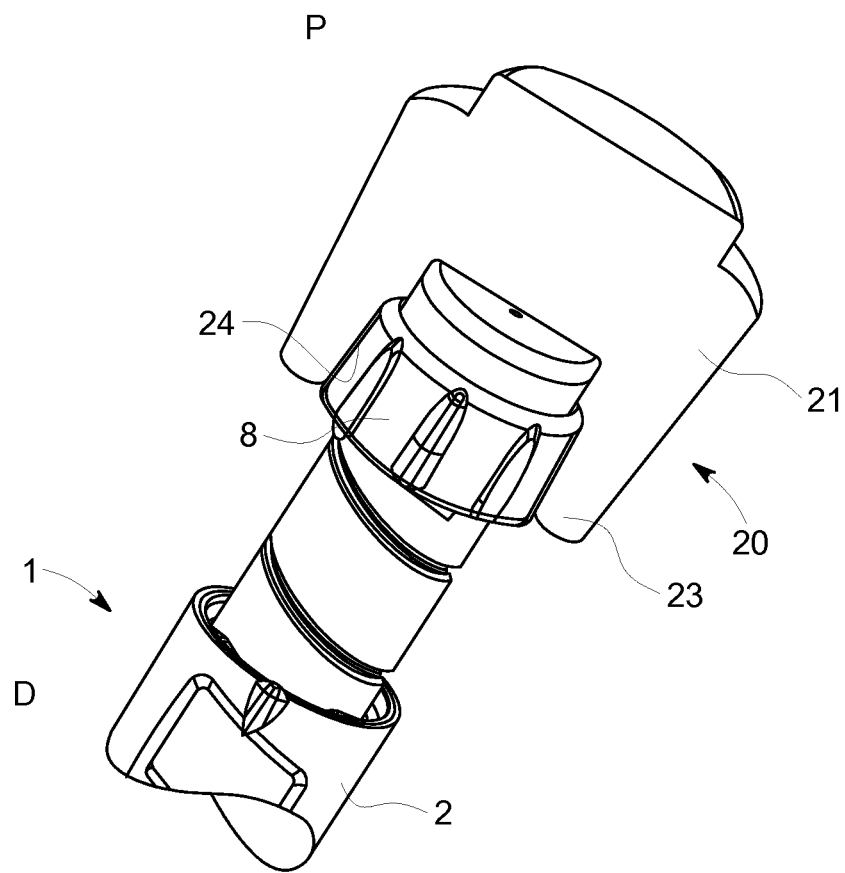
FIG. 3 shows the data collection device attached to the injection device of FIG. 1, with the data collection device shown in cross-section.

FIG. 3 is a cross-sectional view of an example data collection device 20 when attached to the injection device 1. The data collection device 20 includes a housing 21 that includes a sleeve 23 which is placed over the control dial 8. The data collection device 20 is attached to the control dial 8 of the injection device 1 via the sleeve 23. The sleeve 23 defines a cavity 24 in which the control dial 8 is located when the data collection device 20 is attached to the injection device 1. The distal end D of the cavity 24 is open, and the control dial 8 is inserted through the open distal end.

It will be appreciated that FIG. 3 is a simplified illustration of the data collection device 20. In various examples, the data collection device 20 may comprise further parts. For example, the data collection device may include a second part that is movably coupled to the sleeve 23. For example, the second part might rotate or move axially relative to the sleeve 23. The data collection device 20 may include a button that can be depressed relative to the other parts of the data collection device 20. The button may include a spring. However, such a button is not essential. For example, the data collection device 20 may determine use of the injection device 1 if a sensor detects rotation of the control dial. In one embodiment, the data collection device 20 may have a motion sensor such as an accelerometer to detect use of the injection device 1 by, for example, detecting axial and/or rotational movement of the control dial. In another embodiment, the button and motion sensor are omitted and instead the data collection device 20 is constantly powered on.

In addition, the data collection device 20 may include various electronic components. For example, the data collection device 20 may include one or more of a power source, for example a battery, a switch, a processor, a connector, a transmitter, and/or a receiver.

In one example, the data collection device 20 includes a switch arranged to detect axial movement of a part of the data collection device 20, for example a button. In this way, the data collection device 20 can detect use of the injection device 1.

The electronic components may monitor use of the injection device. For example, the data collection device 20 may record or transmit or display information relating to use of the injection device 1, such as dose size, time of dose, number of doses, and the like.

In arrangements, the sleeve 23 is shaped such that there is substantially even engagement between the sleeve 23 and the control dial 8 for the whole of the axial length of the control dial 8. This helps to ensure correct axial orientation of the data collection device 20 with the injection device 1. Axial orientation is provided because the shapes of the components are such that any incorrect orientation results in a corrective force being applied radially between the control dial 8 and the sleeve 23 as they are mated together. Correct axial alignment is useful because it provides a better transmission of rotation force from the sleeve 23 to the control dial 8 and because it provides better feedback to the user when dose delivery is performed. It also generally improves the experience of the user.

To set a medicament dosage amount to be administered, the user may grip and rotate the data collection device 20, since this will cause the control dial 8 of the injection device 1 to turn and, thereby, program the dosage amount.

Figure 4A:
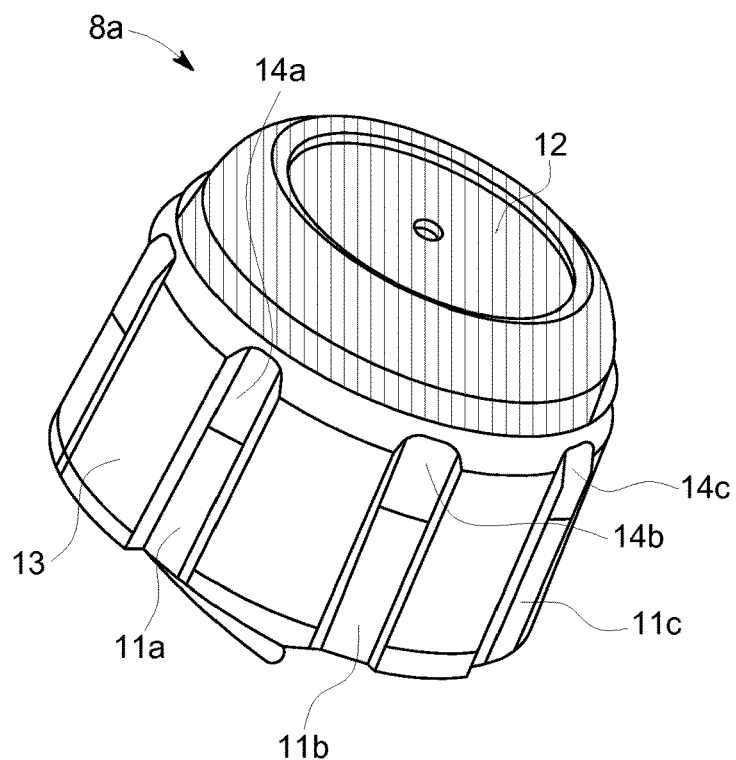
FIGS. 4A and 4B show different example control dials of the injection device of FIG. 1.
Figure 4B:
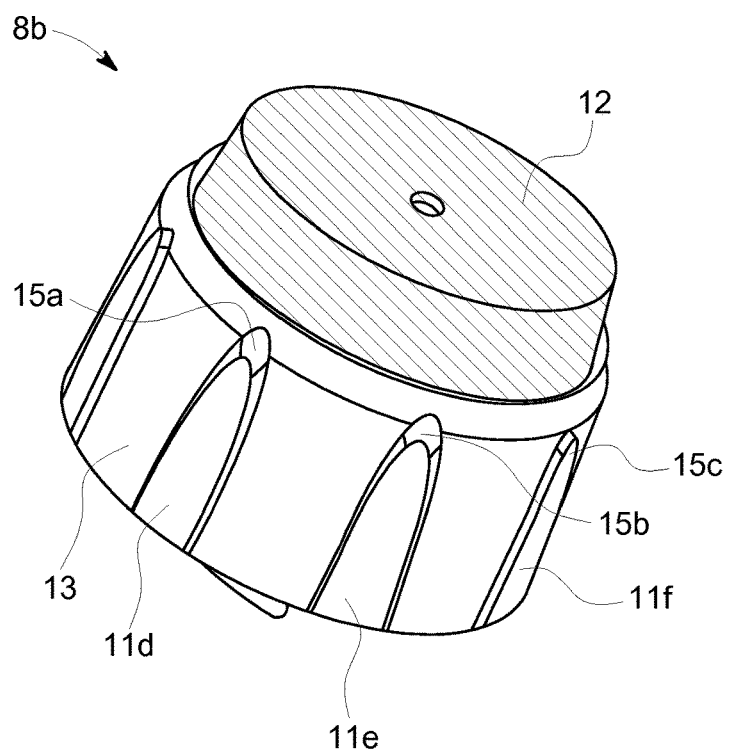

Different injection devices similar to the SoloStar®, or variations of the SoloStar®, may have differently shaped control dials 8. For example, FIG. 4A shows a first control dial 8a and FIG. 4B shows an alternative control dial 8b. Each of the example control dials 8a, 8b includes a dial part 13 and an injection button 12. The dial part 13 has a slightly conical form, tapering towards the injection button 12, which is at the proximal end.

As illustrated, formations 11a, 11b, 11c, 11d, 11e, 11f are formed about the circumferential surface of the dial part 13. The formations 11a, 11b, 11c, 11d, 11e, 11f protrude from the circumferential surface of the dial part 13. The formations 11a, 11b, 11c, 11d, 11e, 11f are spaced about the dial part 13 and extend in an axial direction.

On the example control dial 8a of FIG. 4A, the formations 11a, 11b, 11c have a generally rectangular form with rounded edges and a tapered upper part 14a, 14b, 14c that tapers towards the circumferential surface of the dial part 13.

On the example control dial 8a of FIG. 4A, the formations 11d, 11e, 11f have a generally triangular form and a rounded upper part 15a, 15b, 15c.

The formations 11a, 11b, 11c on control dial 8a differ to the formations 11d, 11e, 11f on the control dial 8b, although the dial part 13 and button 12 are approximately identical.

In some examples, a control dial 8 may include a single formation that is larger than the other formations. For example, the larger formations may act as an indicator to the user of the rotational position of the control dial 8.

In an example, the control dial 8a of FIG. 4A is used on a SoloStar® insulin pen injection device 1 having a first type of medicament, and the control dial 8b of FIG. 4B is used on a SoloStar® insulin pen injection device 1 having a second type of medicament.

Different shape control dials 8a, 8b may be used on different injection devices 1, for example injection devices 1 that contain different medicaments. Or the formations 11 of control dials 8a, 8b from different factories may vary. It is advantageous that the data collection device 20 can fit different types of control dials 8a, 8b, so that the data collection device 20 can be used on different injection devices 1. The examples of the data collection device 20 described hereinafter can attach to the various control dials 8a, 8b while accounting for the variations in the shapes of the formations 11a, 11b, 11c, 11d, 11e, 11f on the control dials 8a, 8b.

Figure 5:
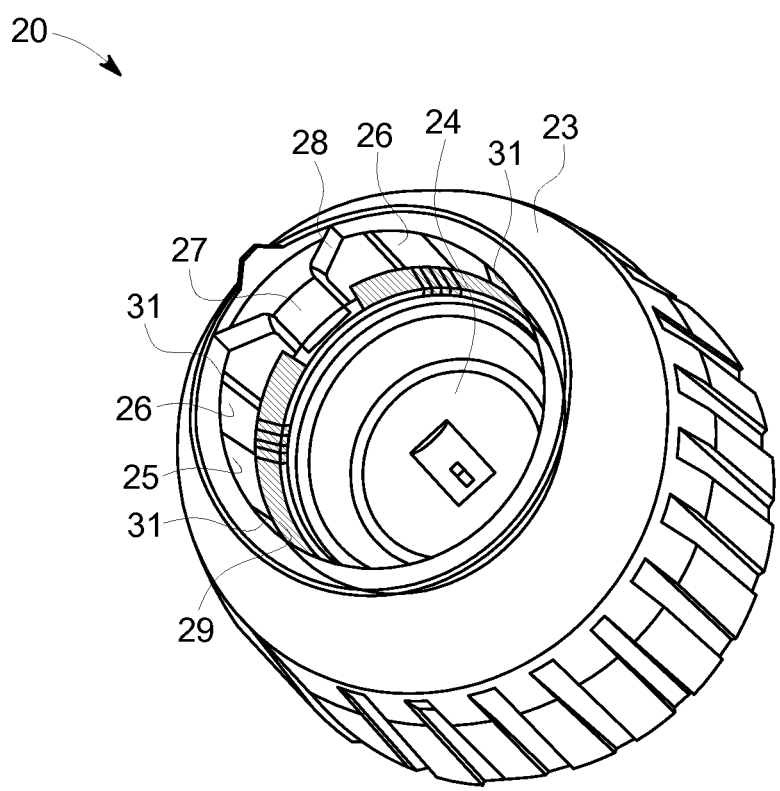
FIG. 5 shows an example data collection device for attachment to the injection device of FIG. 1.

FIG. 5 shows an example data collection device 20 adapted to be fitted to either of the control dials 8a, 8b of FIGS. 4A and 4B, and to other similar control dials of the same or similar injection devices 1.

The data collection device 20 of FIG. 5 comprises a sleeve 23 that defines a cavity 24 extending to the distal end of the data collection device 20 for receiving the control dial 8. The sleeve 23 includes an inner circumferential wall 25 that faces the cavity 24. The inner circumferential wall 25 is adapted to substantially match the outer profile of the various control dials 8a, 8b such that the sleeve 23 fits over the control dials 8a, 8b.

Specifically, the inner circumferential wall 25 is conical, and matches the exterior form of the control dial 8. The inner circumferential wall 25 also includes a plurality of grooves 26. The grooves 26 are large enough to accommodate any of the formations 11a, 11b, 11c, 11d, 11e, 11f on any of the various control dials, for example the control dials 8a, 8b of FIGS. 4A and 4B.

As illustrated in FIG. 5, the inner circumferential wall also includes a wider groove 27, which is adapted to receive a larger formation, such as those described with reference to FIGS. 4A and 4B. The wider groove 27 may include a funnel-shaped mouth 28, as illustrated in FIG. 5. The funnel-shaped mouth 28 can act to rotate the data collection device 20 into rotational alignment with the formations 11a, 11b, 11c, 11d, 11e, 11f on the control dial 8a, 8b as the data collection device 20 is pushed onto the control dial 8a, 8b.

Figure 6A:
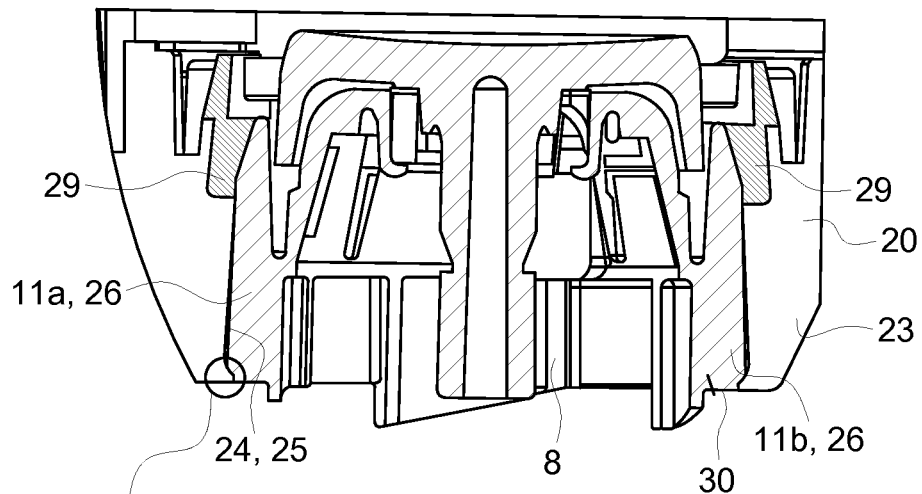
FIGS. 6A and 6B show cross-sectional views of the data collection device of FIG. 5 when it is attached to the injection device of FIG. 1.

As illustrated in FIGS. 5 and 6A, the data collection device 20 also includes a deformable portion 29 positioned to define a part of the inner circumferential wall 25. The deformable portion 29 extends circumferentially around the cavity 24 at a proximal end of the cavity 24. The deformable portion 29 is positioned to grip the formations 11a, 11b, 11c, 11d, 11e, 11f in order to rotationally couple the data collection device 20 to the control dial 8.

FIG. 6A shows the data collection device 20 of FIG. 5 after attachment to the control dial 8. As shown, the control dial 8 is received in the cavity 24 of the sleeve 23, and the inner circumferential wall 25 substantially matches the exterior form of the control dial 8. As also shown, the tops of the formations 11a, 11b on the control dial 8 have engaged the deformable portion 29 in the inner circumferential wall 25. Specifically, the proximal ends of the formations 11a, 11b are in contact with the deformable portion 29.

Figure 6B:
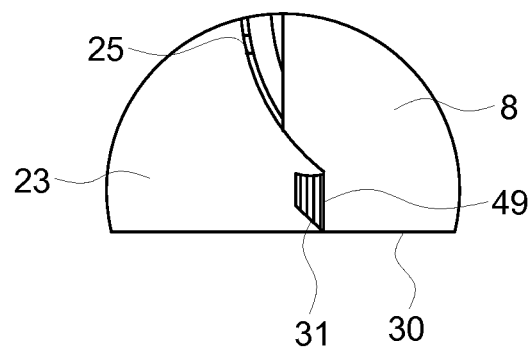

As shown in FIG. 6B, which is an enlarged view of part of FIG. 6A, the inner circumferential wall 25 of the sleeve 23 has an axial attachment member that engages the distal edge 30 of the control dial 8 in a snap-fit arrangement.

Specifically, the inner circumferential wall 25 of the data collection device 20 includes a snap portion 31 positioned at a distal end of the cavity 24. This snap portion 31 is arranged to snap over the distal edge 30 of the control dial 8 when the data collection device 8 is attached to the injection device 1.

In some examples, as illustrated in FIGS. 6A and 6B, the distal edge 30 of the control dial 8 includes a cut-back portion 49 that the snap portion 31 engages with. In other examples, the distal edge 30 of the control dial 8 may be rounded or beveled for engagement with the snap portion 31.

The cut-back portion 49, rounded or beveled distal edge 30 may be formed on the main dial part (13, see FIGS. 4A and 4B) of the control dial 8. Alternatively, the cut-back portion 49, rounded or beveled distal edge 30 may be formed on one or more of the formations 11a, 11b, 11c, 11d, 11e, 11f of the control dial 8.

Figure 7:
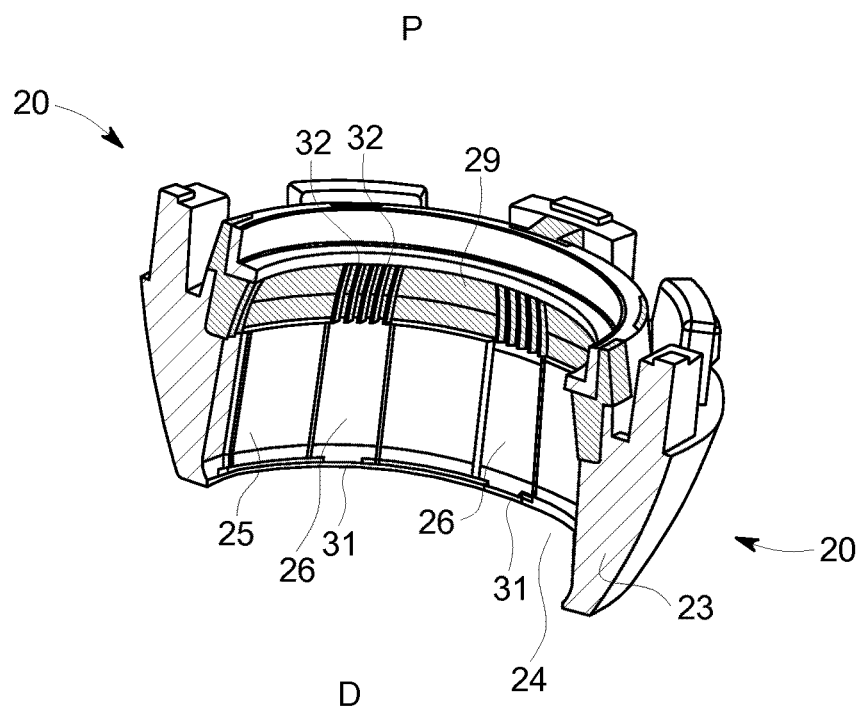
FIG. 7 shows a cross-sectional view of the data collection device of FIG. 5.

In one example, the data collection device 20 has one snap portion 31 per formation 11a, 11b, 11c, 11d, 11e, 11f on the control dial 8, as shown in FIGS. 5 and 7. In other examples, the data collection device 20 has two or more snap portions 31 arranged to engage the distal edges 30 of an equivalent number of the formations 11a, 11b, 11c, 11d, 11e, 11f on the control dial 8. In another example, there is one snap portion 31 per formation 11a, 11b, 11c, 11d, 11e, 11f.

The snap-fit arrangement provided by the one or more snap portions 31 on the data collection device 20 provides axial attachment of the data collection device 20 to the injection device 1, specifically the control dial 8. That is, the snap-fit arrangement holds the data collection device 20 on the control dial 8 in an axial direction. The snap portions 31 can be considered the axial attachment member.

To attach the data collection device 20 to the control dial 8 the grooves 26 are aligned to the formations 11a, 11b, 11c, 11d, 11e, 11f on the control dial 8 and the data collection device 20 is pushed onto the injection device 1. As the data collection device 20 is pushed onto the control dial 8 the snap portions 31 will engage the formations 11a, 11b, 11c, 11d, 11e, 11f on the control dial 8 and will be deflected outwardly as the control dial 8 moves into the cavity 24. Once the control dial 8 is adequately inserted into the cavity 24, the snap portions 31 pass over the distal edge 30 and snap underneath the distal edge 30 of the control dial 8 to engage the control dial 8. This axially attaches the data collection device 20 to the control dial 8.

As described above, in this position the proximal ends of the formations 11a, 11b, 11c, 11d, 11e, 11f on the control dial 8 engage the deformable portion 29. Engagement between the formations 11a, 11b, 11c, 11d, 11e, 11f and the grooves 26, and/or engagement between the formations 11a, 11b, 11c, 11d, 11e, 11f and the deformable portion 29, provides rotational coupling of the data collection device 20 to the control dial 8.

In this way, the data collection device 20 can be axially attached to the control dial 8 and rotationally coupled to the control dial 8. Advantageously, the grooves 26 and the deformable portion 29 do not have to axially attach the data collection device 20 to the control dial 8, because this function is provided by the snap-fit arrangement. Therefore, the grooves 26 and deformable portion 29 can be adapted to fit a wide variety of formations 11a, 11b, 11c, 11d, 11e, 11f, as these features only provide rotational coupling. However it can be appreciated that the deformable portion 29 could be the axial attachment member if required.

As explained hereinafter, the deformable portion 29 may vary so as to better engage with various formations 11a, 11b, 11c, 11d, 11e, 11f on the control dial 8.

FIG. 7 shows a cross-section of the data collection device 20 through the cavity 24. As shown, the inner circumferential wall 25 of the sleeve 26 includes a plurality of grooves 26, each of which has a snap portion 31 for axially attaching the data collection device 20 to the control dial 8, as explained above.

As also shown in FIG. 7, the deformable portion 29 is integrally moulded with the sleeve 23. For example, the sleeve 23 is moulded from a rigid plastics material, such as a thermoplastic material, and the deformable portion 29 is moulded at the same time. Such a dual-moulding process can be achieved using injection moulding, for example. Alternatively, the deformable portion 29 may be glued or welded to the sleeve 23. In other examples, the deformable portion 29 may be trapped between two parts of the data collection device 20 that attach to each other, thereby holding it in positon.

The deformable portion 29 may be made of a flexible, resilient material, for example rubber.

As shown, the deformable portion 29 is disposed at a proximal end P of the cavity 24, to engage the proximal ends of the formations 11a, 11b, 11c, 11d, 11e, 11f on the control dial 8, as previously explained.

The deformable portion 29 includes a ring that extends about the inner circumferential wall 25. Where the deformable portion 29 is coincident with the grooves 26, the deformable portion 29 is provided with ribs 32. In the example of FIG. 7, five ribs 32 are provided per groove 26.

The ribs 32 extend in an axial direction. The ribs 32 are easily deformed by the proximal ends of the formations 11a, 11b, 11c, 11d, 11e, 11f when attaching the data collection device 20 to the control dial 8, and provide rotational coupling between the data collection device 20 and the control dial 8.

Figure 8A:
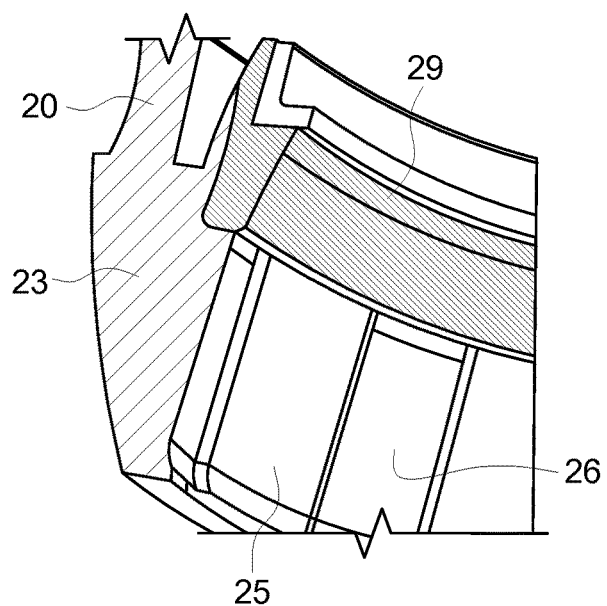
FIGS. 8A to 8C show cross-section views of variations of the data collection device of FIG. 5.
Figure 8B:
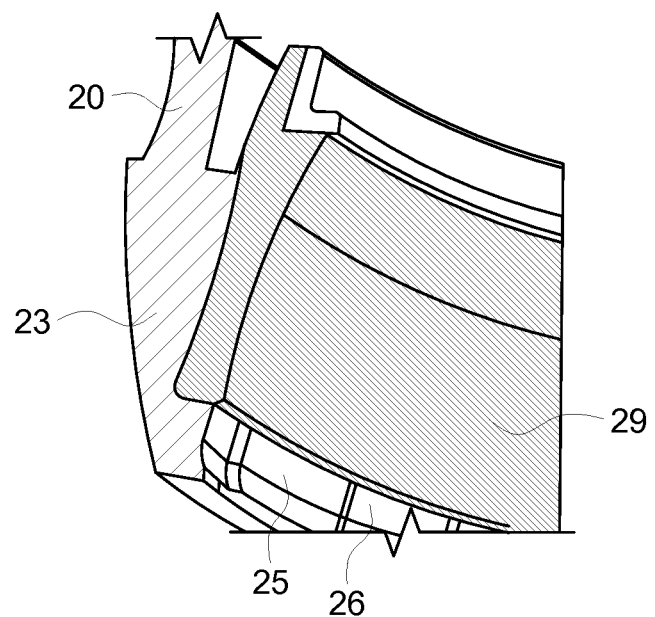
Figure 8C:
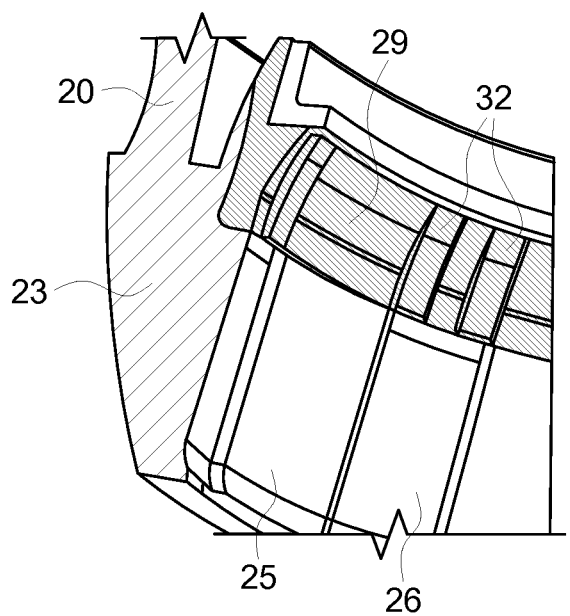

FIGS. 8A to 8C illustrate various alternatives of the deformable portion 29 of the data collection device 20.

In FIG. 8A, the deformable portion 29 is as described with reference to FIG. 7, but without the ribs 32 formed in line with the grooves 26. In this example, the material of the deformable portion 29 may be more malleable (i.e. softer) so that the data collection device 20 can be attached to the control dial 8 without undue force.

In FIG. 8B the deformable portion 29 is longer than in FIG. 8A in the axial direction. The deformable portion 29 of this example extends further in a distal direction, towards the distal end of the sleeve 23. This increased length results in greater interaction between the formations 11a, 11b, 11c, 11d, 11e, 11f and the deformable portion 29, resulting in stronger rotational coupling.

In FIG. 8C the deformable portion 29 is as described with reference to FIG. 7, but the ribs 32 that are coincident with the grooves 26 are wider in the circumferential direction. The wider ribs 32 may require more force to deform to permit the data collection device 20 to connect to the control dial 8, but provide stronger rotational coupling between the data collection device 20 and the control dial 8.

Figure 9A:
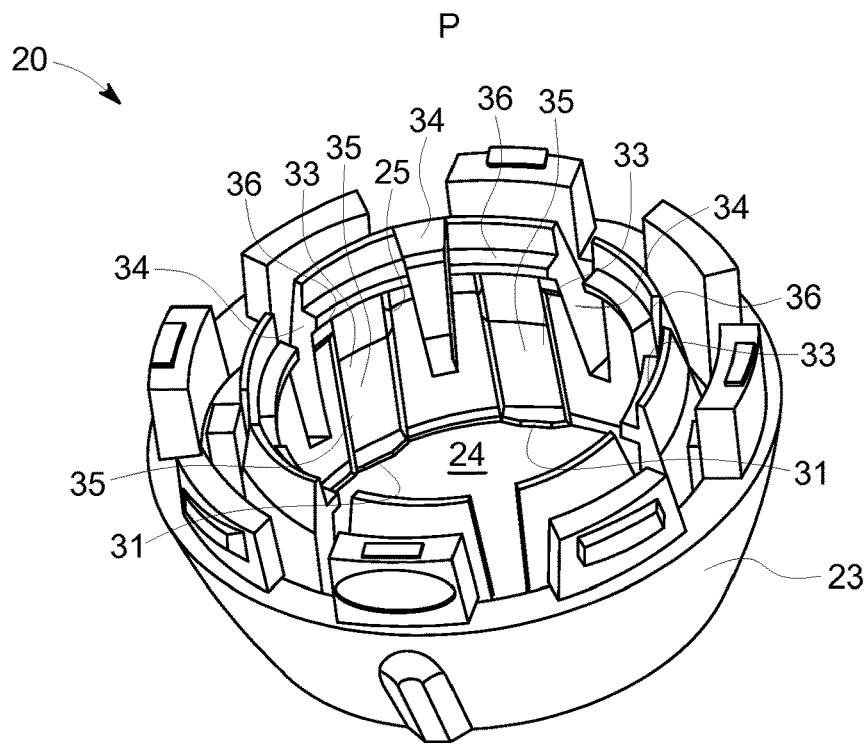
FIG. 9A shows a further example data collection device for attachment to the injection device of FIG. 1.
Figure 9B:
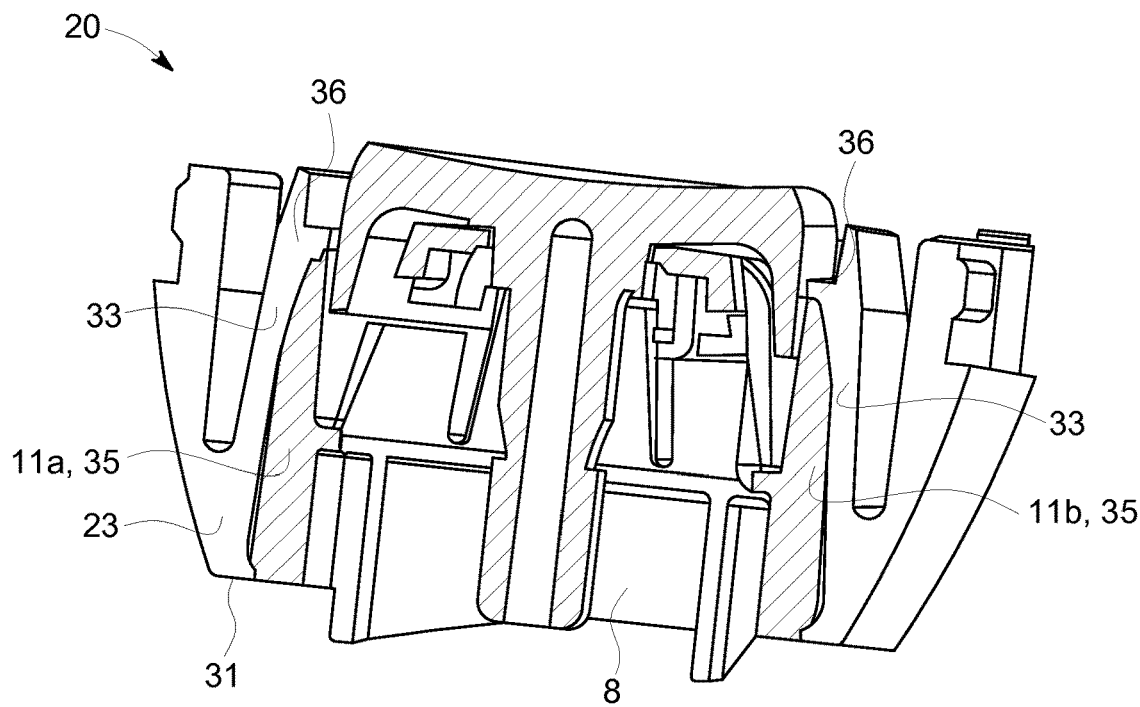
FIG. 9B shows a cross-sectional view of the data collection device of FIG. 9A when it is attached to the injection device of FIG. 1.

FIGS. 9A and 9B show a further example of a data collection device 20 for attachment to a control dial 8 of an injection device 1. In this example, the sleeve 23 axially attaches to the control dial 8 via a snap-fit attachment.

In this example, the inner circumferential wall 25 of the sleeve 23 is formed of a plurality of arms 33. Slots 34 are provided between the arms 33 in the inner circumferential wall 25, extending from the proximal end top towards the open distal end of the cavity 24.

Each arm 33 has a recess 35 on its inner surface adapted to receive a formation 11a, 11b, 11c, 11d, 11e, 11f of the control dial 8. Snap portions 31 are provided at the distal end of the arms 33, in the same location as the examples of FIGS. 5 to 8C. These snap portions 31 are arranged to engage with a distal edge 30 of the control dial 8, for example the distal ends of the formations 11a, 11b, 11c, 11d, 11e, 11f, as described with reference to FIGS. 6A and 6B.

As illustrated in FIGS. 9A and 9B, proximal snap portions 36 are provided at the proximal ends of the recesses 35. The proximal snap portions 36 are positioned to engage with the proximal ends of the formations 11a, 11b, 11c, 11d, 11e, 11f on the control dial 8.

The proximal ends of the formations 11a, 11b, 11c, 11d, 11e, 11f may be rounded, chamfered, or cut-back to allow the proximal snap portions 36 to engage therewith.

To attach the data collection device 20 to the control dial 8 the data collection device 20 is pushed onto the control dial 8. As the data collection device 20 is pushed axially the control dial 8 deflects the snap portions 31. As the control dial 8 engages the proximal snap portions 36 the arms 33 may be deflected outwards. Once the control dial 8 is fully inserted the snap portions 31 engage the distal edge 30 of the control dial 8, as previously explained, and the proximal snap portions 36 engage the proximal ends of formations 11a, 11b, 11c, 11d, 11e, 11f. In this position, the snap portions 31, 36 axially attach the data collection device 20 to the control dial 8. Snap portions 31, 36 can be considered the axial attachment member. In addition, the formations 11a, 11b, 11c, 11d, 11e, 11f are disposed in the recesses 35, thereby rotationally coupling the data collection device 20 to the control dial 8.

The slots 34 between the arms 33 permit the arms 33 to be deflected outwards, allowing the proximal snap portions 36 to move into the engaged position, and allowing the formations 11a, 11b, 11c, 11d, 11e, 11f to move into the recesses 35.

In the examples of FIGS. 5 to 9B the snap portions 31, 36 are deflected from an initial position into an engagement position as the data collection device 20 is pushed onto the control dial 8.

Figure 10:
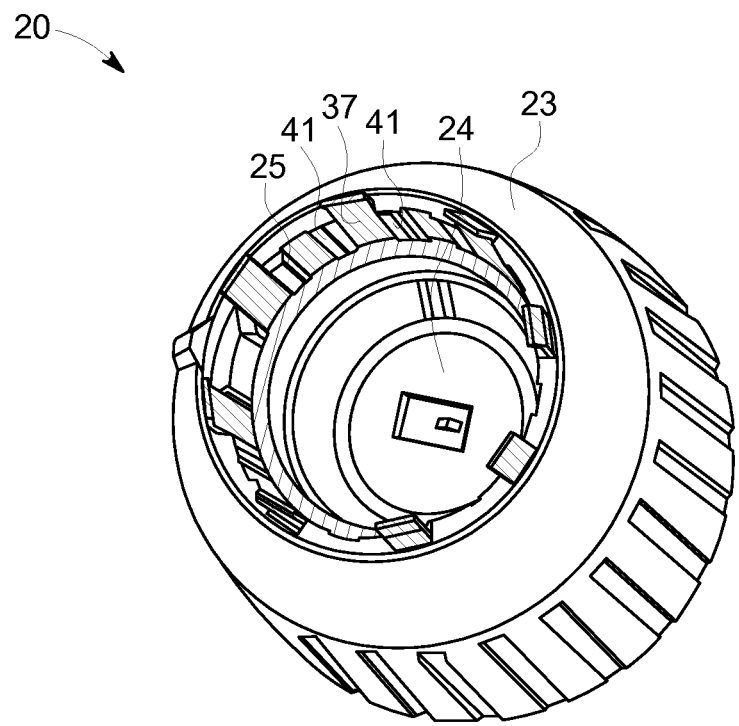
FIG. 10 shows a further example data collection device for attachment to the injection device of FIG. 1.
Figure 11:
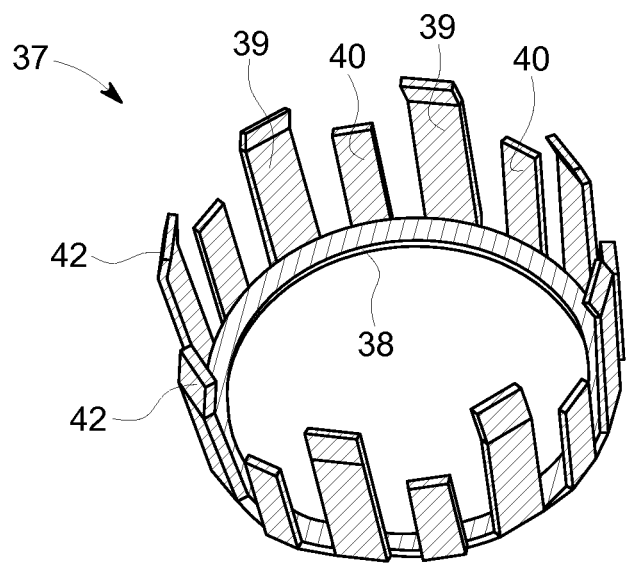
FIG. 11 shows an attachment member of the data collection device of FIG. 10.
Figure 12:
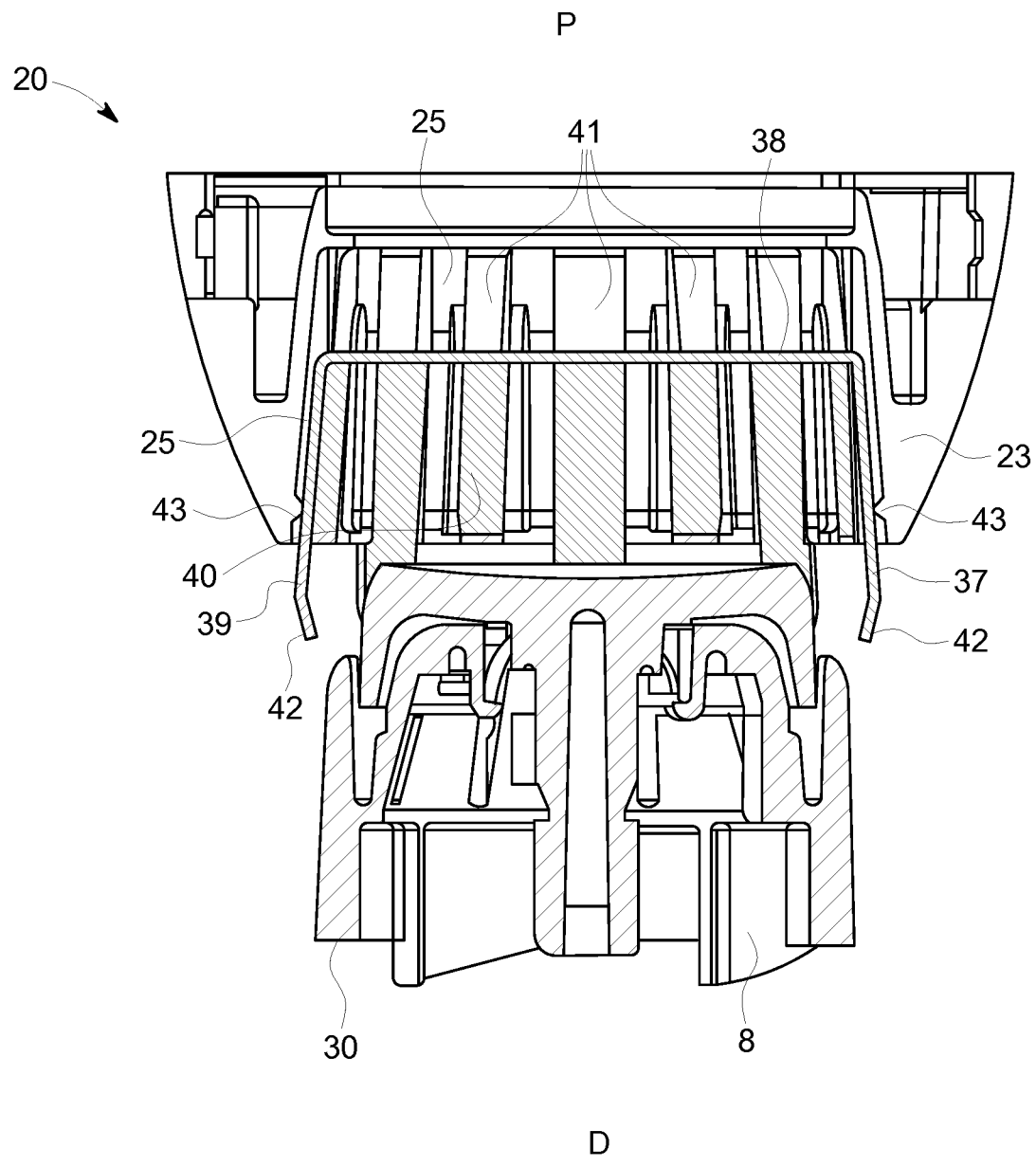
FIG. 12 shows a cross-sectional view of the data collection device of FIG. 10 with the attachment member of FIG. 11 and the injection device of FIG. 1.

FIGS. 10, 11 and 12 show a further example of a data collection device 20 adapted to be fitted to a control dial 8, for example the control dials 8a, 8b of FIGS. 4A and 4B, and to other similar control dials 8.

In this example, the data collection device 20 includes a sleeve 23 having a circumferential wall 25 that defines a cavity 24 in which the control dial 8 is received. As illustrated, a gripping member is arranged within the cavity 24. In this example, the gripping member is a clamp 37 which grips the control dial 8 to connect the data collection device 20 to the control dial 8. The clamp 37 has a base ring 38 and a plurality of arms 39, 40 protruding from the base ring 38. The arms 39, 40 are spaced from each other. The base ring 38 is disposed proximally in the cavity 24, with the arms 39, 40 extending distally from the base ring 38.

The arms 39, 40 are arranged to tighten against the control dial 8 as the control dial 8 is pushed into the cavity 24 and the clamp 37 moves axially in a proximal direction. In this embodiment the clamp 37 can be considered the axial attachment member.

The clamp 37 includes long arms 39 and short arms 40, alternately arranged about the clamp 37. The long arms 39 are arranged such that they are disposed between the formations 11a, 11b, 11c, 11d, 11e, 11f on the control dial 8 when the data collection device 20 is attached to the control dial 8. The short arms 40 are arranged to overlie the formations 11a, 11b, 11c, 11d, 11e, 11f on the control dial 8 when the data collection device 20 is attached to the control dial 8.

As also illustrated, the circumferential wall 25 includes a plurality of grooves 41 that are arranged to receive the arms 39, 40 of the clamp 37. The grooves 41 that correspond to the short arms 40 are further adapted to receive the formations 11a, 11b, 11c, 11d, 11e, 11f on the control dial 8.

As shown, the distal ends 42 of the long arms 39 are inwardly bent.

The inner circumferential wall 25 of the sleeve 23 includes one or more protrusions 43 at the distal end of the cavity 24. The protrusion 43 may be a circumferential ridge that extends about the inner circumferential wall 25 of the sleeve 23, or the inner circumferential wall 25 may have a plurality of discrete protrusions 43 that are aligned with the long arms 39.

Figure 13A:
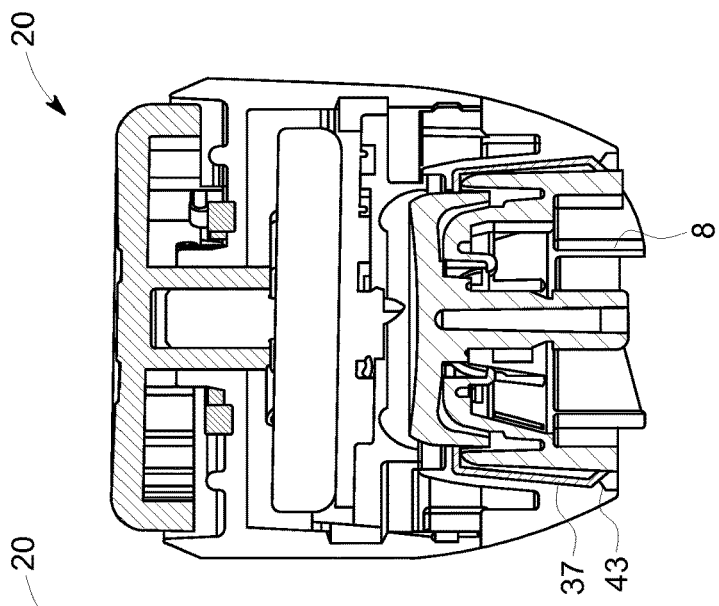
FIGS. 13A to 13C show cross-sectional views of the data collection device of FIG. 10 in the process of being attached to the injection device of FIG. 1.
Figure 13B:
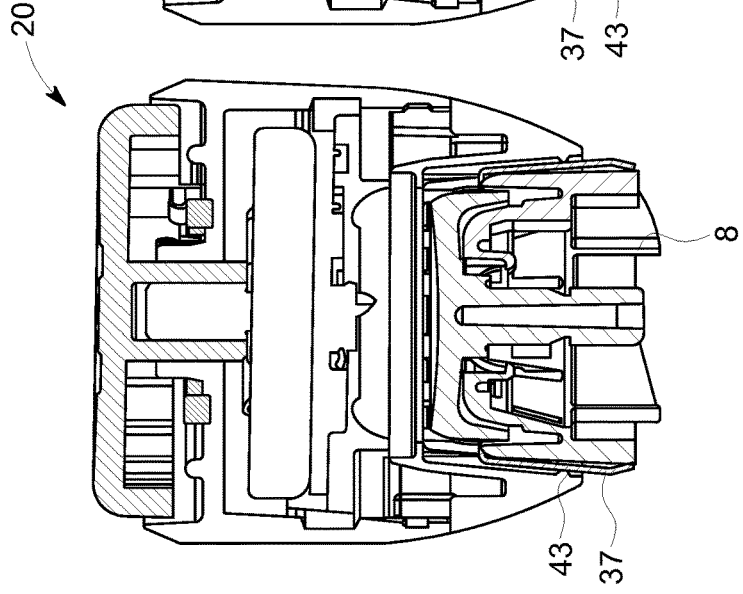
Figure 13C:
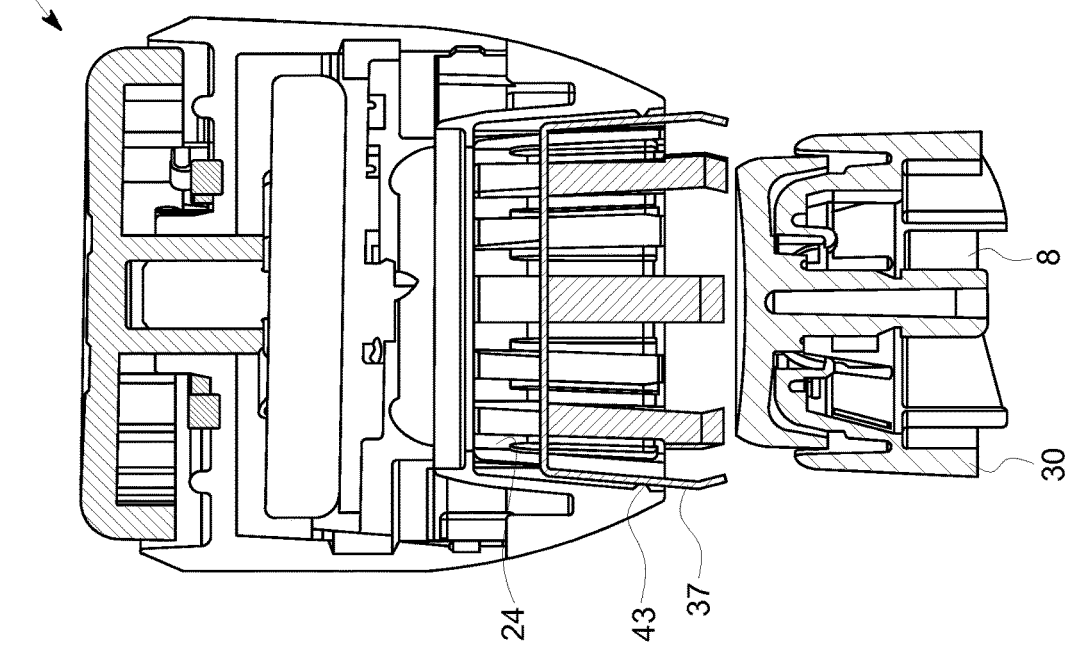

FIGS. 13A to 13C illustrate the process of attaching the data collection device 20 of FIGS. 10 to 12 to the control dial 8. As shown in FIG. 13A, the clamp 37 is in an initial position and is partly received in the cavity 24 and the arms 39, 40 are in a non-deflected state, open enough to receive the control dial 8 between the arms 39, 40, as shown in FIG. 13B. As the control dial 8 is pressed into the cavity 24, as illustrated in FIG. 13B, the internal shape of the cavity 24 deflects the arms 39, 40 inwardly to an engagement position to grip the control dial 8. In the position illustrated in FIG. 13C the control dial 8 is fully inserted into the cavity 24, and the arms 39, 40 are gripping the control dial 8.

The protrusions 43 in the inner circumferential wall 25 interact with the inwardly deflected ends 42 of the long arms 39 in such a way as to retain the clamp 37 and control dial 8 in the cavity 24. Specifically, as the control dial 8 is pushed into the cavity 24 the long arms 39 are slightly straightened at the deflected ends 42, allowing the bend in each long arm 39 to move proximally above the protrusions 43. Once past the protrusions 43 the long arms 39 move back out again, effectively locking the clamp 37 into the cavity.

In the position in FIG. 13C, the formations 11a, 11b, 11c, 11d, 11e, 11f on the control dial 8 and the short arms 40 of the clamp 37 are in the grooves 41. The short arms 40 may be arranged to be deflected as the control dial 8 is pressed into the cavity 24, thereby exerting an inward gripping force on the formations 11a, 11b, 11c, 11d, 11e, 11f. Similarly, in the position of FIG. 13C the long arms 39 of the clamp 37 are slightly deflected and thereby exert an inward gripping force on the control dial 8. In some examples, the deflected ends 42 of the long arms 39 may extend underneath the distal end 30 of the control dial 8.

In this way, the data collection device 20 is axially attached to the control dial 8 by the arms 39, 40 of the clamp 37. In addition, the grooves 41 that receive the formations 11a, 11b, 11c, 11d, 11e, 11f rotationally couple the data collection device 20 to the control dial 8.

Figure 14:
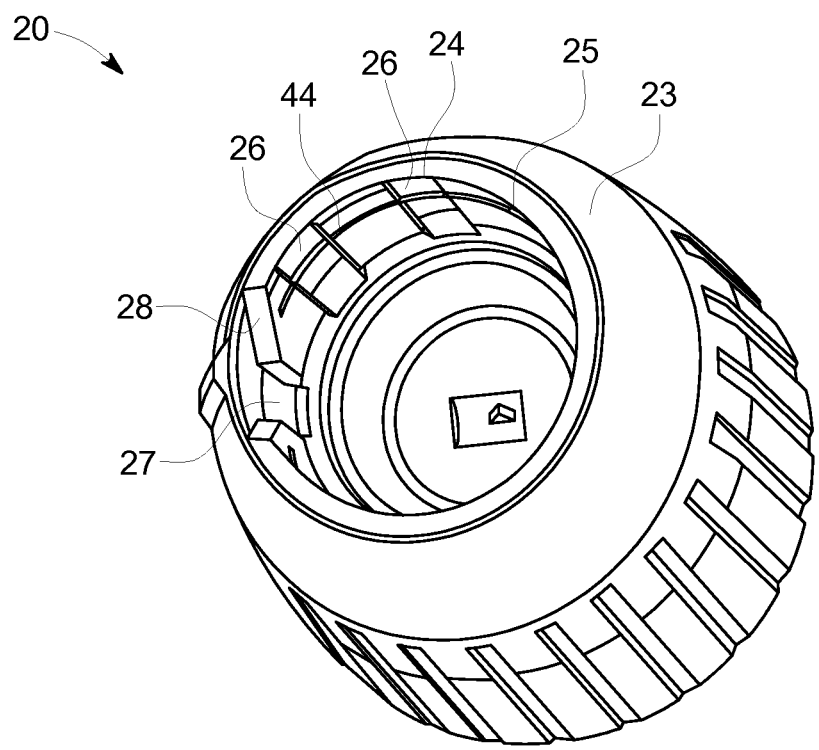
FIG. 14 shows a further example data collection device for attachment to the injection device of FIG. 1.
Figure 15:
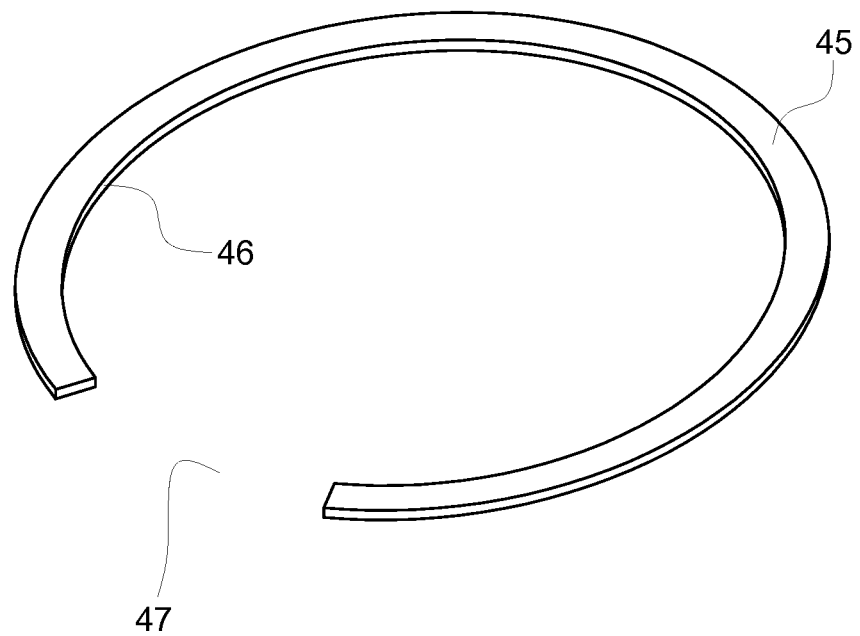
FIG. 15 shows an attachment member of the data collection device of FIG. 14.
Figure 16:
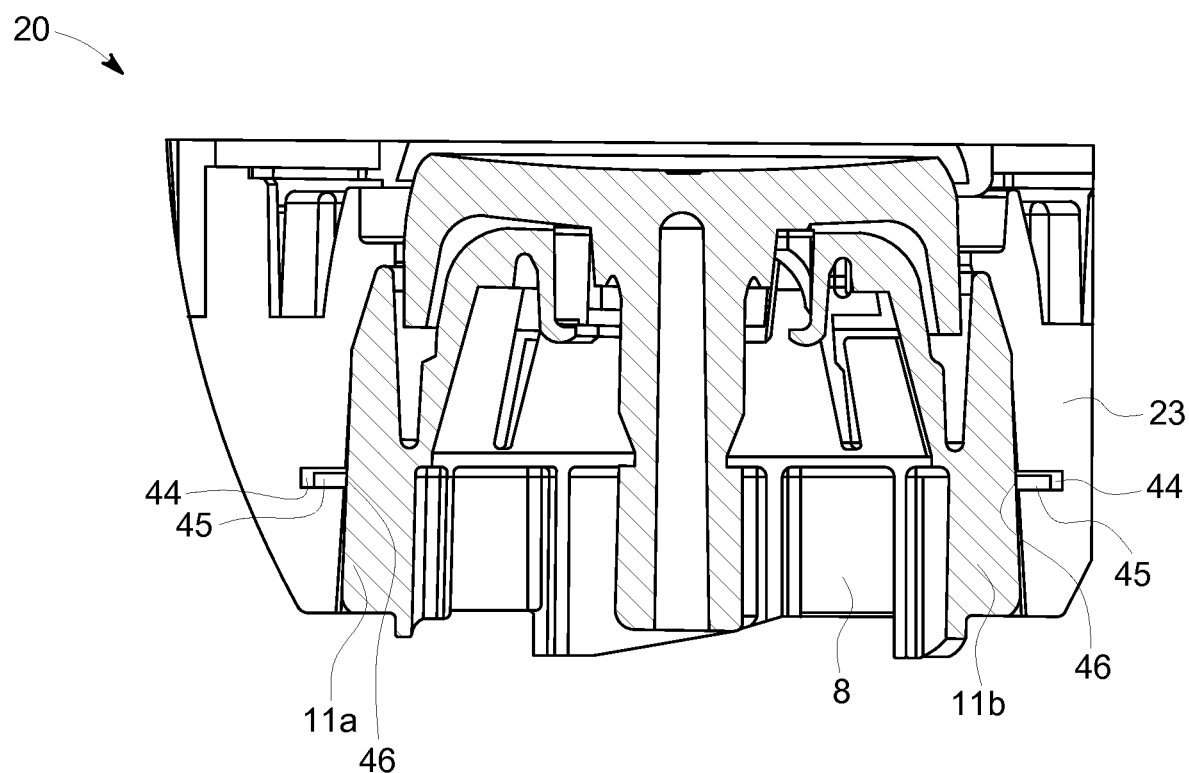
FIG. 16 shows a cross-sectional view of the data collection device of FIG. 14 attached to the injection device of FIG. 1.

FIGS. 14, 15 and 16 show a further example of a data collection device 20 adapted to be fitted to either of the control dials 8a, 8b of FIGS. 4A and 4B, and to other similar control dials 8.

In this example, the data collection device 20 includes a sleeve 23 having an inner circumferential wall 25 that defines cavity 24 in which the control dial 8 is received. In this example, the inner circumferential wall 25 has a circumferentially extending groove 44. The groove 44 is arranged to receive an attachment ring 45, which is illustrated in FIG. 15 and visible in position in FIG. 16.

As shown in FIG. 16, the attachment ring 45 is disposed in the groove 44 such that an inner edge 46 of the attachment ring 45 extends out of the groove 44 into the cavity 24. In this way, the inner edge 46 engages the control dial 8 when the control dial 8 is pressed into the cavity 24.

The attachment ring 45 comprises a resilient material and includes a gap 47. In an initial position the attachment ring 45 extends into the cavity 24, and as the control dial 8 is pressed into the cavity 24 the attachment ring 45 deforms outwardly under the force of the control dial 8. In response, the resilience of the attachment ring 45 causes the inner edge 46 to grip the control dial 8, thereby axially attaching the data collection device 20 to the control dial 8. In this position, the attachment ring 45 is in an engagement position. The attachment ring 45 in this instance can be considered the axial attachment member.

The resilience of the attachment ring 45 and/or the design of the inner edge 46 may be such that the attachment ring 45 grips the control 8 or cuts into the control dial 8. The attachment ring 45 will grip or cut into the formations 11a, 11b, 11c, 11d, 11e, 11f of the control dial 8, as they are the outermost features of the control dial. It can be appreciated that the attachment ring could also provide characteristics to be the rotational coupling member.

As illustrated in FIG. 14, the inner circumferential surface 25 of the sleeve 23 also includes grooves 26, similar to those described with reference to FIG. 5, that receive the formations 11a, 11b, 11c, 11d, 11e, 11f on the control dial 8 and provide rotational coupling between the data collection device 20 and the control dial 8. A wider groove 27, with optional funnel-shaped mouth 28, may be provided to accommodate a larger formation.

Figure 17A:
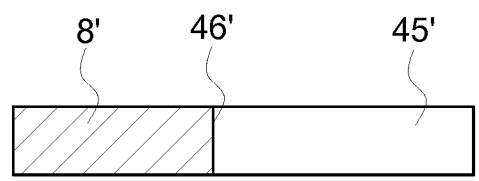
FIGS. 17A and 17B show cross-sectional views of an edge of the attachment member of FIG. 15.
Figure 17B:
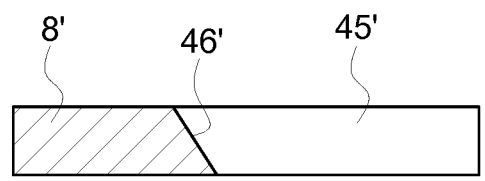

As illustrated in FIG. 17A, the inner edge 46' of the attachment ring 45' may be square, and the resilient force of the attachment ring 45' presses against the control dial 8' to provide the axial attachment. Alternatively, as shown in FIG. 17B, the inner edge 46' of the attachment ring 45' may be angled to provide a cutting edge that cuts into the control dial 8' to provide the axial attachment.

Figure 18:
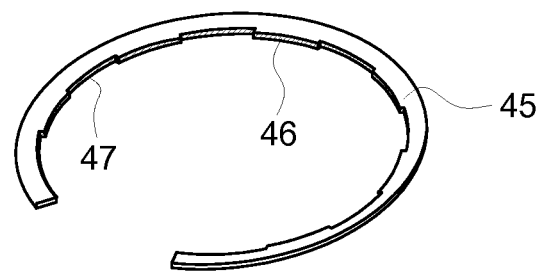
FIG. 18 shows an alternative example attachment member for the data collection device of FIG. 14; and, FIGS. 19A and 19B show alternative example attachment members for the data collection device of FIG. 14.

As shown in FIG. 18 the inner edge 46 of the attachment ring 45 may be stepped, with recesses 47 provided to accommodate the formations 11a, 11b, 11c, 11d, 11e, 11f on the control dial 8. In this way, the attachment ring 45 may grip or cut into the formations 11a, 11b, 11c, 11d, 11e, 11f and the main part of the control dial 8 between the formations 11a, 11b, 11c, 11d, 11e, 11f.

Figure 19A:
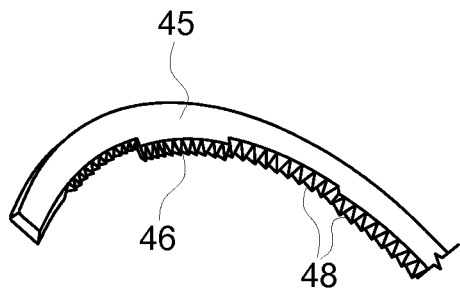
Figure 19B:
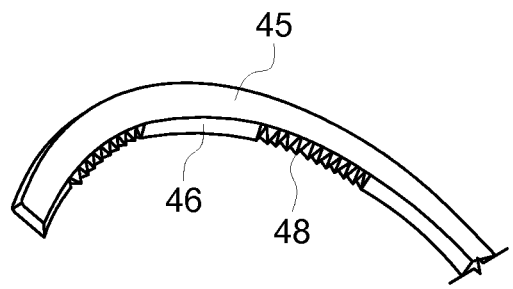

As shown in FIGS. 19A and 19B the inner edge 46 of the attachment ring 45 may be provided with serrations 48 to increase the gripping or cutting force provided by the resilient force of the attachment ring 45 pressing against the control dial 8. As shown in FIG. 19A, the serrations 48 may be provided on a stepped attachment ring 45, such as that of FIG. 18. Alternatively, the serrations 48 may be provided on a circular attachment ring 45, such as that shown in FIG. 15. Alternatively, as shown in FIG. 19B, the serrations 48 may be arranged into spaced groups about the attachment ring 45.

It can be appreciated that in each of the described examples any features that can provide axial attachment can be considered the axial attachment member and any features that can provide rotational coupling can be considered the rotational coupling member.

The axial attachment member prevents the data collection device from disconnecting from the control dial whilst the rotational coupling member can provide for the data collection device moving in unison with the control dial.

In each of the described examples the data collection device 20 is adapted to be used on a variety of similar control dials 8, such as the control dials 8a, 8b described with reference to FIGS. 4A and 4B.

The injection device 1 is configured to inject or infuse a medicament into a patient. For example, delivery could be sub-cutaneous, intra-muscular, or intravenous. Delivery could be needleless. The injection device 1 could be operated by a patient or care-giver, such as a nurse or physician, and may be one of various types of safety syringe, pen-injector, or auto-injector. The injection device 1 can include a cartridge-based system that requires piercing a sealed ampule before use. Volumes of medicament delivered with these various devices can range from about 0.5 ml to about 2 ml. The injection device 1 may be a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml). In combination with a specific medicament, the injection device 1 may also be customized in order to operate within required specifications. For example, the injection device 1 may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, the injection device 1 may include a hollow needle ranging from about 25 to about 31 Gauge in size. Common sizes are 27 and 29 Gauge.

The injection device 1 can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of such an injection device 1 may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to allow injection of a medicament to be provided. The injection device 1 may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. The injection device 1 may also require a specific sequence of steps to cause the one or more automated functions to occur. The injection device 1 may operate with a sequence of independent steps.

The injection device 1 can include one or more functions of a safety syringe, pen-injector, or auto-injector. For example, the injection device 1 may include a mechanical energy source configured to automatically inject a medicament (as typically found in an auto-injector) and a dose setting mechanism (as typically found in a pen-injector).

The injection device 1 may be disposable or it may be reusable.

The injection device 1 may provide a fixed dose or a user-settable dose.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30)

human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A supplementary device for an injection device, the injection device comprising a control dial that is rotatably mounted about an axis at a proximal end of the injection device, wherein the supplementary device comprises:
   a sleeve adapted to be positioned over the control dial when the supplementary device is attached to the injection device; and,
   an axial attachment member disposed within the sleeve and arranged such that insertion of the control dial into the sleeve moves the axial attachment member from an initial position that permits axial movement of the control dial into the sleeve, into an engagement position in which the axial attachment member engages the control dial to attach the supplementary device to the control dial,
   wherein the axial attachment member comprises a clamp having a base ring and a plurality of arms extending distally from the base ring;
   wherein in the initial position the control dial can move between the arms;
   wherein in the engagement position the arms are pressed against said control dial for axial attachment of the supplementary device to the injection device; and
   wherein the arms abut an inner circumferential surface of the sleeve such that an axial movement of the clamp within and relative to the sleeve moves the arms radially inward towards a longitudinal axis from the initial position to the engagement position.

2. The supplementary device of claim 1, wherein the axial attachment member in the engagement position is adapted to engage the control dial such that axial movement of the control dial relative to the sleeve is restricted.

3. The supplementary device of claim 1, further comprising a rotational coupling member arranged to rotationally couple the sleeve to the control dial such that rotation of the supplementary device causes rotation of the control dial.

4. The supplementary device of claim 3, wherein the axial attachment member and the rotational coupling member are a single component of the supplementary device.

5. The supplementary device of claim 3, wherein the control dial comprises one or more axially extending formations protruding from the control dial, and wherein the rotational coupling member comprises one or more grooves arranged to engage the one or more formations to rotationally couple the sleeve to the control dial.

6. The supplementary device of claim 5, wherein the one or more grooves are adapted to receive formations having different sizes and/or shapes such that the supplementary device can be used with various injection devices.

7. The supplementary device of claim 5, wherein the one or more formations comprise multiple formations having different sizes.

8. The supplementary device of claim 5, wherein the one or more grooves are configured for rotating the sleeve into alignment with the one or more formations protruding from the control dial.

9. The supplementary device of claim 1, wherein the axial attachment member is arranged to engage a distal edge of the control dial.

10. The supplementary device of claim 1, wherein the base comprises a base ring, the plurality of arms protruding from the base ring having distal ends thereof configured to be deflected inwardly such that in the engagement position the distal ends of the arms press against the control dial.

11. The supplementary device of claim 1, wherein a diameter of the attachment member is reduced in the engagement position relative to a diameter of the attachment member in the initial position.

12. The supplementary device of claim 1, further comprising a sensor to detect rotation of the control dial.

13. The supplementary device of claim 1, wherein the sleeve comprises an inner circumferential wall that is conical.

* * * * *